(12) United States Patent
Tsuda

(10) Patent No.: US 9,377,516 B2
(45) Date of Patent: Jun. 28, 2016

(54) METHOD FOR ADJUSTING MAGNETIC RESONANCE IMAGING APPARATUS AND SUPERCONDUCTIVE MAGNET EXCITATION DOCK

(71) Applicant: Munetaka Tsuda, Tokyo (JP)

(72) Inventor: Munetaka Tsuda, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 186 days.

(21) Appl. No.: 14/057,535

(22) Filed: Oct. 18, 2013

(65) Prior Publication Data

US 2014/0043030 A1    Feb. 13, 2014

Related U.S. Application Data

(62) Division of application No. 13/375,005, filed as application No. PCT/JP2010/059608 on Jun. 7, 2010, now Pat. No. 8,726,489.

(30) Foreign Application Priority Data

Jun. 11, 2009    (JP) ................. 2009-140276

(51) Int. Cl.
*H01F 6/00*     (2006.01)
*G01R 33/38*    (2006.01)
(Continued)

(52) U.S. Cl.
CPC .............. *G01R 33/3802* (2013.01); *G01R 3/00* (2013.01); *G01R 33/36* (2013.01);
(Continued)

(58) Field of Classification Search
CPC .................................. G01R 33/3815

USPC .......................................... 335/216
See application file for complete search history.

(56) References Cited

U.S. PATENT DOCUMENTS 4,209,657 A * 6/1980 Inai ................... F25D 3/10
174/15.4
4,342,932 A   8/1982 Glebov et al.
(Continued)

FOREIGN PATENT DOCUMENTS

JP    59-163809    9/1984
JP    60-164374    8/1985
(Continued)

OTHER PUBLICATIONS

International Search Report in PCT/JP2010/059608.

*Primary Examiner* — Alexander Talpalatski
(74) *Attorney, Agent, or Firm* — Cooper & Dunham LLP

(57) ABSTRACT

An adjustment method of a magnetic resonance imaging apparatus includes: a cooling and excitation step in which work of transporting a superconducting magnet to a facility different from a facility where the superconducting magnet is to be installed, cooling a superconducting coil of the superconducting magnet with a refrigerant, and supplying a current from an external power supply for excitation is repeated until a predetermined rated current flows; a demagnetization and transportation step of demagnetizing the superconducting coil and transporting the superconducting magnet to the facility where the superconducting magnet is to be installed in a state where the superconducting coil is cooled by the refrigerant; and an installation step of installing the superconducting magnet in the facility where the superconducting magnet is to be installed and supplying a predetermined rated current from an external power supply to the superconducting coil in order to excite the superconducting coil.

4 Claims, 5 Drawing Sheets

(51) Int. Cl.
  *G01R 33/3815* (2006.01)
  *H01F 6/02* (2006.01)
  *G01R 3/00* (2006.01)
  *G01R 33/36* (2006.01)
  *A61B 5/055* (2006.01)
  *H01F 6/04* (2006.01)

(52) U.S. Cl.
  CPC ....... *G01R 33/3804* (2013.01); *G01R 33/3815* (2013.01); *H01F 6/02* (2013.01); *A61B 5/055* (2013.01); *H01F 6/04* (2013.01); *Y10T 29/49002* (2015.01); *Y10T 29/4902* (2015.01); *Y10T 29/49004* (2015.01); *Y10T 29/49005* (2015.01); *Y10T 29/4908* (2015.01); *Y10T 29/49014* (2015.01)

(56) References Cited

U.S. PATENT DOCUMENTS

| | | | |
|---|---|---|---|
| 4,625,520 A * | 12/1986 | Yagi | F17C 3/085 220/901 |
| 4,800,354 A | 1/1989 | Laskaris | |
| 4,808,954 A | 2/1989 | Ito | |
| 5,563,369 A | 10/1996 | Yazawa et al. | |
| 5,598,710 A * | 2/1997 | Tomeoku | H01F 6/00 62/48.1 |
| 5,680,085 A * | 10/1997 | Aihara | H01L 39/20 335/216 |
| 5,711,157 A * | 1/1998 | Ohtani | F25B 9/10 62/467 |
| 5,782,095 A | 7/1998 | Chen | |
| 5,802,855 A * | 9/1998 | Yamaguchi | F25B 21/02 505/700 |
| 6,109,042 A * | 8/2000 | Woods | F17C 13/12 62/51.1 |
| 6,504,373 B2 * | 1/2003 | Tsuda | G01R 33/3815 324/318 |
| 7,263,839 B2 * | 9/2007 | Overweg | F25D 29/001 62/259.2 |
| 7,928,321 B2 | 4/2011 | Corsaro et al. | |
| 2006/0137376 A1 * | 6/2006 | Overweg | F25D 29/001 62/259.2 |
| 2007/0214821 A1 | 9/2007 | Astra | |
| 2007/0247263 A1 | 10/2007 | Calvert et al. | |
| 2008/0179784 A1 | 7/2008 | Calvert | |

FOREIGN PATENT DOCUMENTS

| | | |
|---|---|---|
| JP | 63-289909 | 11/1988 |
| JP | 2-150003 | 6/1990 |
| JP | 5-62827 | 3/1993 |
| JP | 11-243007 | 9/1999 |
| JP | 2006-324411 | 11/2006 |
| JP | 2007-271254 | 10/2007 |
| JP | 2008-147666 | 6/2008 |

* cited by examiner

METHOD FOR ADJUSTING MAGNETIC RESONANCE IMAGING APPARATUS AND SUPERCONDUCTIVE MAGNET EXCITATION DOCK

CROSS-REFERENCE TO RELATED APPLICATIONS

This application is a divisional of U.S. patent application Ser. No. 13/375,005, filed Nov. 29, 2011 as a Section 371 National Stage of PCT/JP2010/059608 filed Jun. 7, 2010, claiming the priority of Japanese Patent Application No. 2009-140276 filed with The Japanese Patent Office on Jun. 11, 2009.

TECHNICAL FIELD

The present invention relates to a magnetic resonance imaging (hereinafter, referred to as MRI) using a superconducting magnet and in particular, to an MRI apparatus using a superconducting magnet which generates a high magnetic field with high energy.

BACKGROUND ART

MRI apparatuses are widely spread in medical facilities similarly to diagnostic apparatuses using X-rays. The reason is that the MRI apparatus has a different function from the diagnostic apparatus using X-rays. Not only the diagnostic apparatus using X-rays but also the MRI apparatus is an indispensable diagnostic apparatus for more reliable examination in diagnosis. The diagnostic function of the MRI apparatus is to obtain not only the morphological image information but also the functional diagnostic information. For example, the MRI apparatus can clearly draw a cerebral infarction lesion in the early stage of the disease. In particular, in an MRI apparatus using a magnet with high magnetic field performance in which the magnetic field strength exceeds 1 tesla and the magnetic field homogeneity is 3 ppm or less, many new diagnostic functions have been developed taking advantage of the magnetic field performance so that actual clinical applications are made.

In order to achieve the high diagnostic function of the MRI apparatus, it is necessary to increase the magnetic field strength of the imaging space where a subject is disposed and to increase the magnetic field homogeneity. The increase in the magnetic field strength increases the strength of a nuclear magnetic resonance (NMR) signal detected from an examination area. Accordingly, since a signal-to-noise ratio or a contrast-to-noise ratio of a diagnostic image is increased, the quality of the diagnostic image is improved. In addition, the increase in the signal-to-noise ratio indicates that a high-speed imaging technique for shortening an examination time becomes possible. On the other hand, since even a slight difference in resonance frequencies of NMR signals acquired from the examination area can be identified by increasing the magnetic field homogeneity, the spatial resolution of the diagnostic image or the analytical capability of spectral diagnosis can be improved.

In order to acquire a high-quality examination result in a diagnostic image or the like, not only the performance of the MRI apparatus but also realizing a comfortable examination environment, which relieves the tension of the subject, is important. In order to improve the examination environment, an open MRI apparatus with an open-structure imaging space where a subject is disposed has been realized (PTL 1). In the MRI apparatus of PTL 1, an open examination space is realized by using a superconducting magnet in which superconducting coils are disposed above and below the space, in which a subject is disposed, interposed therebetween.

On the other hand, in a superconducting coil formed by pouring thermosetting resin (epoxy resin) between wound superconducting wires and curing it, distortion by cooling occurs due to a difference between the thermal contraction rates of the superconducting wires and the resin, as disclosed in PTL 2. If the superconducting wires move by several micrometers due to this distortion, the superconducting wires are locally heated. As a result, a quench by which a change to the normal conducting state is made occurs, as is known well. If a quench occurs in the superconducting magnet of the MRI apparatus, not only does the superconducting magnet not function as a superconducting magnet any more, but also a large amount of refrigerant is vaporized by the heating and is emitted through en emergency exhaust port. For this reason, it is necessary to avoid the occurrence of a quench in the MRI apparatus installed in the hospital and the like.

In order to avoid the sudden occurrence of a quench in an MRI apparatus which holds a persistent current over a long period of time, PTL 2 proposes reducing distortion energy generated in superconducting wires and resin by repeating the electromagnetic force generated at the time of excitation and demagnetization several times (at least 3 times) or an adjustment method of a superconducting magnet which releases distortion energy of a superconducting coil by causing a quench forcibly with the heat from the outside.

CITATION LIST

Patent Literature

[PTL 1] WO2002/071942A1
[PTL 2] JP-A-2006-324411

SUMMARY OF INVENTION

Technical Problem

The effect of an adjustment method of a superconducting magnet disclosed in PTL 2 is accepted in a superconducting magnet with a relatively low magnetic field strength, which has a static magnetic field strength of 1 tesla or less and in which a current flowing as a persistent current when operating the superconducting magnet is set as a much lower value than the maximum current (this is called a critical current) flowing through superconducting wires.

However, if the value of the persistent current flowing through the superconducting wires is increased in order to increase the static magnetic field strength, distortion cannot be released in the adjustment method disclosed in PTL 2. This is because energy of the electromagnetic force generated by a compulsory quench or excitation and demagnetization disclosed in PTL 2 is calculated as about $\frac{1}{10}$ of distortion energy generated at the time of cooling of superconducting wires and resin and this is too small to release total distortion energy. For this reason, if a high magnetic field superconducting magnet is adjusted by the method disclosed in PTL 2, distortion remains. Accordingly, a problem occurs in that a quench occurs in the high magnetic field superconducting magnet even with slight disturbance (heating due to movement of a superconducting coil or the influence of a magnetic field) which does not cause a quench in a low magnetic field superconducting magnet.

In particular, since a superconducting magnet used in the open MRI apparatus has a complicated structure in which superconducting coils are disposed up and down with the imaging space interposed therebetween, the superconducting magnet is easily influenced by cooling distortion or electromagnetic force distortion. Accordingly, since the number of times of quench required until the distortion is completely released at the time of adjustment tends to increase, it takes time to release the cooling distortion.

Hereinafter, causing a quench in order to release distortion is called training. In addition, the number of quench required until distortion is released is called the number of times of training.

Another cause of making difficult the operation of completely releasing the cooling distortion energy of the superconducting magnet is that the required number of times of training can not be predicted in the current technology. For this reason, it is difficult to decide a construction period until the superconducting magnet can be used after being transported to medical facilities, as in the related art. On the other hand, it is preferable to shorten the period of a process of installing a superconducting magnet in medical facilities in order to shorten the duration of the examination service suspended.

In addition, at the time of training, a superconducting coil generates heat by a quench, and a large amount of liquid helium (for example, tens of thousands of liters due to training performed multiple times) evaporates. Then, helium gas which is 700 times the liquid helium is generated to cool the air, and the water vapor in the air rises like white smoke. For this reason, if training is performed in a hospital or near the hospital, hospital employees or neighboring residents may mistake it for fire.

However, if training is performed at the location distant from the hospital, it is necessary to transport the superconducting magnet to the hospital. Accordingly, even in a superconducting magnet determined that the distortion was completely released, training may be necessary due to distortion at the time of re-cooling when the temperature of the superconducting coil is increased and cooled again at the time of transportation.

In addition, there is also a problem of cost because a large amount of liquid helium evaporates in training. Until the distortion is completely released, it is necessary to cause a quench multiple times. As an example, this requires tens of thousands of liters of liquid helium, which costs.

The invention has been made in view of the above, and it is an object of the invention to provide a cooling and excitation method of a superconducting magnet capable of deciding and shortening the installation period after transportation to medical facilities.

Solution to Problem

In order to solve the above-described problem, in a first aspect of the invention, the following adjustment method of an MRI apparatus including a superconducting magnet is provided.

That is, this is an adjustment method of an MRI apparatus including: a cooling and excitation step in which work of transporting a superconducting magnet manufactured in advance to a facility for excitation different from a facility where the superconducting magnet is to be installed and temporarily installing the superconducting magnet, cooling a superconducting coil of the superconducting magnet with a refrigerant, and supplying a current from an external power supply for excitation is repeated until a predetermined rated current flows; a demagnetization and transportation step of demagnetizing the superconducting coil excited by the rated current as a preliminary step and transporting the superconducting magnet to the facility where the superconducting magnet is to be installed in a state where the superconducting coil is cooled by the refrigerant; and an installation step of installing the superconducting magnet in the facility where the superconducting magnet is to be installed and supplying a predetermined rated current from an external power supply to the superconducting coil in order to excite the superconducting coil. Thus, since the cooling and excitation step is performed in the facility for excitation, distortion of the superconducting coil can be eliminated (training) by causing a quench, the number of times of which is not decided and the number of times of which until the rated current flows is not known, in the facility for excitation. After the demagnetization, the superconducting magnet is transported in a cooled state. Accordingly, in the installation step performed in the facility where the superconducting magnet is to be installed, it is not necessary to perform the training again. As a result, it is possible to decide and shorten a time required for the installation step.

When a plant for condensing helium gas to liquid helium, a frame on which the superconducting magnet is mounted, a supply pipe used to send liquid helium from the plant to the superconducting magnet, and a recovery pipe used to send helium gas from the superconducting magnet to the plant are provided in the facility for excitation, the liquid helium can be directly supplied from the plant to the superconducting magnet. Therefore, it is possible to reduce the cost in transporting helium. In addition, the helium gas discharged from the superconducting magnet can be recovered and reused.

In the cooling and excitation step, for example, current value is increased with a predetermined increase rate when supplying a current from the external power supply to the superconducting coil. When a quench occurs in the superconducting coil and the refrigerant evaporates, training is performed using a method of injecting a refrigerant and increasing a value of a current from the external power supply with a predetermined current value increase rate.

In the cooling and excitation step, preferably, the external power supply is separated to make a closed loop in which a persistent current flows after the rated current flows through the superconducting coil, and the state is maintained for a predetermined time. By confirming that a quench does not occur during the state maintained, it is possible to confirm that distortion is released (end of training).

In the demagnetization and transportation step, it is preferable to transport the superconducting coil while maintaining the superconducting coil at a liquid helium temperature or less after the demagnetization.

In the demagnetization and transportation step, it is possible to store the superconducting coil for a predetermined number of days while maintaining the superconducting coil at a liquid helium temperature or less after the demagnetization. In the storage, it is preferable to execute at least one of an operation of a cryocooler of the superconducting magnet and refrigerant supplementation. Moreover, in the storage, it is preferable to operate the cryocooler and a cryoheater of the superconducting magnet in order to maintain the pressure in a refrigerant vessel of the superconducting magnet in a fixed range.

When the temperature of the superconducting coil rises by a predetermined value or more in the demagnetization and transportation step, distortion may occur again in the superconducting coil at the time of re-cooling. Accordingly, it is preferable to increase a current, which is supplied from the external power supply at the time of excitation in the installation step, with a predetermined current value increase rate and perform the training.

In addition, according to a second aspect of the invention, the following adjustment method of an MRI apparatus including a superconducting magnet is provided.

That is, this is an adjustment method of an MRI apparatus including: a training step of performing training for releasing distortion occurring in a superconducting coil by transporting a superconducting magnet manufactured in advance to a facility for excitation different from a facility where the superconducting magnet is to be installed and temporarily installing the superconducting magnet, cooling the superconducting coil of the superconducting magnet with a refrigerant, and supplying a current from an external power supply; a demagnetization and transportation step of demagnetizing the superconducting coil after the training as a preliminary step and transporting the superconducting magnet to the facility where the superconducting magnet is to be installed in a state where the superconducting coil is cooled by the refrigerant; and an installation step of installing the superconducting magnet in the facility where the superconducting magnet is to be installed and supplying a predetermined rated current from an external power supply to the superconducting coil in order to excite the superconducting coil.

In addition, according to a third aspect of the invention, a dock for superconducting magnet excitation which is used for adjustment of an MRI apparatus is provided.

That is, this is a dock for superconducting magnet excitation including: a plant for condensing helium gas to liquid helium; a frame on which a superconducting magnet is mounted; a supply pipe used to send liquid helium from the plant to the superconducting magnet; a recovery pipe used to send helium gas from the superconducting magnet to the plant; a power supply for supplying an excitation current to the superconducting magnet; and a power lead which connects the power supply to the superconducting magnet. By providing such a dock, the superconducting magnet can be cooled and excited at low cost at the place directly connected with the helium plant. In addition, helium gas evaporating in the event of a quench can be recovered and reused.

Preferably, at least two recovery pipes with different diameters used to send the helium gas from the superconducting magnet to the plant are disposed, and the recovery pipe with a large diameter is connected to an emergency exhaust hole for exhausting helium gas, which evaporates in the superconducting magnet in the event of a quench, to the outside. Then, even if a large amount of liquid helium evaporates at once in the event of a quench at the time of training, it can be recovered through the recovery pipe with a large diameter.

Preferably, a constant-pressure valve which is opened when the pressure in the recovery pipe exceeds predetermined pressure is provided in the recovery pipe with a large diameter. In addition, it is preferable to include a fan for diffusing helium gas emitted when the constant-pressure valve is opened. Being mistaken for a fire or the like can be avoided by diffusing white smoke caused by the helium gas.

As a fourth aspect of the invention, the following adjustment method of an MRI apparatus including a superconducting magnet is provided.

That, this is an adjustment method of an MRI apparatus including: a first transportation step of transporting a superconducting magnet manufactured in advance to a facility for excitation different from a facility where the superconducting magnet is to be installed; a second transportation step of repeating work of cooling the superconducting magnet with a refrigerant and exciting the superconducting magnet with a current supplied from an external power supply in the facility for excitation until a predetermined rated current flows and then transporting the superconducting magnet to the facility where the superconducting magnet is to be installed in a state where the superconducting coil demagnetized as a preliminary step is cooled by the refrigerant; and an installation step of installing the superconducting magnet in the facility where the superconducting magnet is to be installed and supplying a predetermined rated current from an external power supply to a superconducting coil in order to excite the superconducting coil.

In addition, according to a fifth aspect of the invention, the following adjustment method of an MRI apparatus including a superconducting magnet is provided.

That is, this is an adjustment method of an MRI apparatus including: a cooling and excitation step in which work of transporting a superconducting magnet manufactured in advance to a facility for excitation and temporarily installing the superconducting magnet, cooling a superconducting coil of the superconducting magnet with a refrigerant, and supplying a current from an external power supply for excitation is repeated until a predetermined rated current flows; and a demagnetization and transportation step of demagnetizing the superconducting coil excited by the rated current as a preliminary step and transporting the superconducting magnet to the facility where the superconducting magnet is to be installed in a state where the superconducting coil is cooled by the refrigerant.

Advantageous Effects of Invention

The following effects are obtained by the adjustment method of an MRI apparatus of the invention.

(1) A superconducting magnet after completion of training of a superconducting magnet can be transported to the medical facilities.

(2) A training process a required time for which is not decided can be eliminated from the installation period, and it is possible to shorten the installation period. In particular, when the current MRI apparatus in the medical facilities is replaced with an open MRI apparatus using a superconducting magnet which has a high magnetic field strength and a release structure, the duration of the current examination service suspended can be minimized.

(3) The supply of helium needed at the time of cooling, excitation, and training becomes easy. Thus, since the facility of the helium plant can be utilized for recovery of helium, there is an effect of cost reduction.

DESCRIPTION OF EMBODIMENTS

Hereinafter, an excitation method of a superconducting magnet of an MRI apparatus of an embodiment of the invention will be described.

<Entire Configuration of an MRI Apparatus>

Figure 1:
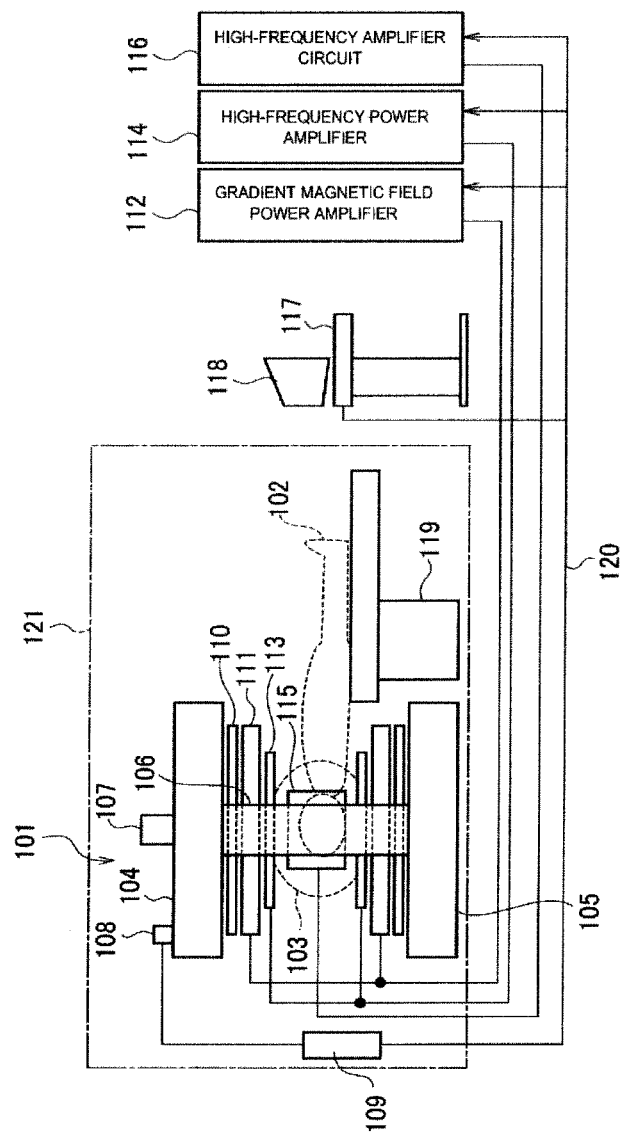
FIG. 1 is a block diagram showing the entire configuration of an MRI apparatus of the invention.

First, the configuration of an MRI apparatus excited in the present embodiment will be described. FIG. 1 shows the entire configuration in a state where the MRI apparatus excited in the present embodiment is installed in the medical facilities. This MRI apparatus uses an open-structure superconducting magnet 101 shown in FIG. 2 as a magnet which generates a static magnetic field. The MRI apparatus is configured to include a gradient magnetic field coil 111, a high-frequency coil 113, a shim plate 110, a moving table 119 on which a subject 102 is carried, a magnet control unit 109, a gradient magnetic field power amplifier 112, a high-frequency power amplifier 114, a high-frequency amplifier circuit 116, a computer 117, and a display 118.

Figure 2:
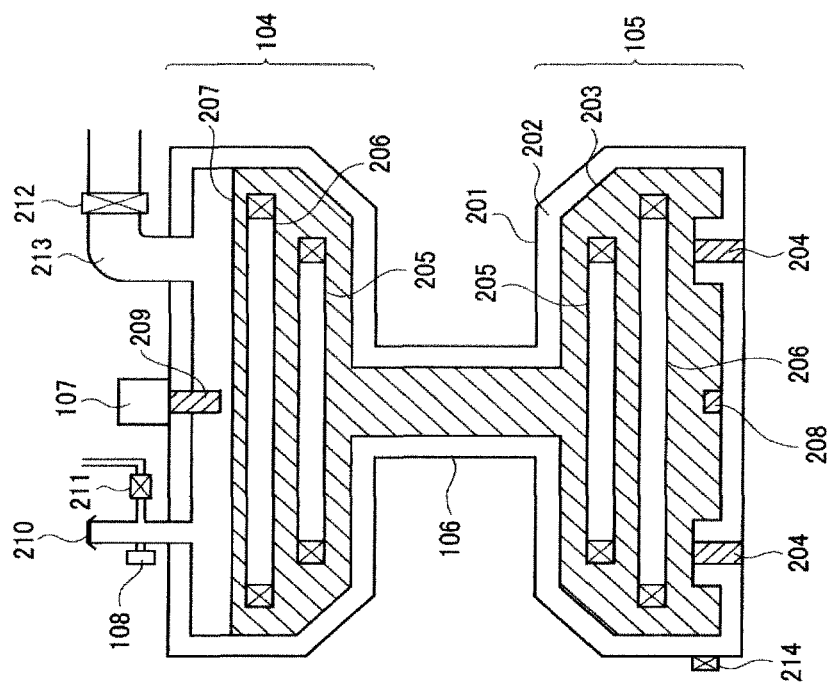
FIG. 2 a sectional view showing the structure of a superconducting magnet of the MRI apparatus shown in FIG. 1.

As shown in FIGS. 1 and 2, the open-structure superconducting magnet 101 includes an upper cryostat 104 and a lower cryostat 105 which are located up and down with an imaging space 103, on which the subject 102 is disposed, interposed therebetween and each of which has superconducting coils 205 and 206 as sources of magnetomotive force therein. The upper cryostat 104 and the lower cryostat 105 are connected to each other by a connection tube 106 as a strut. Accordingly, since an open structure in which front, back, left, and right parts of the imaging space 103 are opened widely is obtained, it is possible to ease the feeling of pressure given to the subject 102. As a result, it is possible to provide the comfortable examination environment for the subject 102.

This superconducting magnet 101 includes a cryocooler 107. Helium gas vaporized within the upper cryostat 104 and the lower cryostat 105 is cooled by the cryocooler 107 and returns to the upper cryostat 104 again as liquid helium. Accordingly, a fully sealed cryostat is formed. In this way, the superconducting magnet 101 suppresses consumption of liquid helium which cools the superconducting coils 205 and 206.

In addition, a plurality of temperature sensors or pressure sensors (not shown in drawings) for monitoring the operation state are provided in the superconducting magnet 101, and the connection terminal 108 is connected to the magnet control unit 109.

The superconducting magnet 101 generates a stable static magnetic field with a magnetic field strength of 1 tesla in the imaging space 103. In order to improve the magnetic field homogeneity to a predetermined value or less, a pair of shim plates 110 are fixed to surfaces of the upper cryostat 104 and the lower cryostat 105 facing the imaging space 103. A plurality of screw holes (not shown in drawings) are open in the shim plate 110, and magnetic screws are mounted at appropriate positions. By correcting the distribution of magnetic flux generated by the superconducting magnet 101 with magnetic flux of the magnetic screws, the magnetic field homogeneity is adjusted to targeted 3 ppm or less.

A pair of gradient magnetic field coils 111 which generate a gradient magnetic field are disposed on surfaces of the shim plates 110 facing the imaging space 103. This gradient magnetic field coil 111 is designed and manufactured in the flat structure so as not to interfere with the open structure of the superconducting magnet 101. In each of the pair of upper and lower gradient magnetic field coils 111, three kinds of coils of x, y, and z coils which generate gradient magnetic fields in three axial directions perpendicular to each other are laminated. The gradient magnetic field power amplifier 112 which applies a current independently is connected to each of the x, y, and z coils.

For example, an operation of the z coil will be described. For example, if a "+" current is applied from the gradient magnetic field power amplifier 112 to upper and lower z coils, the upper z coil generates magnetic flux in the same direction as magnetic flux generated by the superconducting magnet 101, and magnetic flux with the opposite direction to this is generated in the lower z coil. As a result, a gradient magnetic field whose magnetic flux density decreases gradually from top to bottom of the Z axis (vertical axis) of the imaging space 103 is formed. Similarly, the x and y coils form gradient magnetic fields of X and Y axes (both horizontal axes), respectively. Thus, a gradient magnetic field in a predetermined axial direction is superimposed on the magnetic field generated by the superconducting magnet 101.

A pair of high-frequency coils 113 are fixed to the side of the gradient magnetic field coil 111 facing the imaging space 103. This high-frequency coil 113 has a flat structure so as not to interfere with the open structure of the superconducting magnet 101. The high-frequency power amplifier 114 is connected to the pair of upper and lower high-frequency coils 113 so that a high-frequency current is supplied. Then, an examination area of the subject 102 is irradiated with a high-frequency magnetic field with a predetermined frequency, so that nuclear magnetic resonance is generated in the nuclear spin of the examination area. In the case of the present embodiment, a 42 MHz high-frequency magnetic field which causes nuclear magnetic resonance of hydrogen nuclei with a magnetic field strength of 1 tesla is generated. By combining the gradient magnetic field formed by the gradient magnetic field coil 111 with this high-frequency magnetic field, a nuclear magnetic resonance phenomenon is selectively caused in the hydrogen nuclei of the examination area of the subject 102. Then, in a process for which the nuclear spin attenuates while performing precession, three-dimensional position information can be added to the precession.

A detection coil 115 which detects the precession of the nuclear spin is disposed in the examination area of the subject 102. This detection coil 115 detects the precession of the nuclear spin as an electrical signal and passes it to the high-frequency amplifier circuit 116 connected thereto. The high-frequency amplifier circuit 116 converts the detection signal into a digital signal by amplification and detection.

The computer 117 converts the detection signal converted into the digital signal into an image or the like which is to be supplied for medical diagnosis and stores it in a storage device (not shown in drawings) in the computer 117 and also displays it on the display 118. The computer 117 is made to have an advanced diagnostic function according to the high performance characteristics of the superconducting magnet 101 described above. For example, this is a diffusion-weighted echo planar imaging function, a spectral analysis function, or the like.

In addition, the computer 117 controls an operation of each unit through a bus line 120. That is, each of the magnet control unit 109, the gradient magnetic field power amplifier 112, the high-frequency power amplifier 114, and the high-frequency amplifier circuit 116 is connected to the computer 117. The computer 117 controls each unit as programmed and records a state of each unit, and remote monitoring through a communication control device (not shown in drawings) is possible.

As another main unit, the moving table 119 which transports the subject 102 to the center of the imaging space 103 is provided on the front surface of the superconducting magnet 101. The superconducting magnet 101 and the moving table 119 are installed in an examination room 121 which is electromagnetically shielded.

Next, the structure of the superconducting magnet 101 will be further described using FIG. 2.

The outermost shell of the superconducting magnet 101 is a vacuum chamber 201 formed of 10-mm-thick stainless steel, for example. A helium vessel 203 formed of 15-mm-thick stainless steel is provided in the vacuum chamber 201 with a vacuum layer 202 interposed therebetween. A plurality of support bodies 204 are disposed between the helium vessel 203 and the vacuum chamber 201. The support body 204 is formed of FRP (fiber reinforced plastic) resin, which has low heat conductivity and a high strength, so that heat of the vacuum chamber 201 is not transferred to the helium vessel 203.

A pair of main superconducting coils 205 and a pair of shielded superconducting coils 206 are disposed in the helium vessel 203, and the helium vessel 203 is filled with liquid helium 207. A current flows through the pair of upper and lower main superconducting coils 205 to generate a magnetic field with a strength of 1 tesla in the imaging space 103, and a current flows through the pair of upper and lower shielded superconducting coils 206 so that magnetic flux leaking to the outside of the vacuum chamber 201 is canceled out. Through this configuration, the density of magnetic flux leaking to the outside of the examination room 121 can also be suppressed to 5 mT, which is the management criteria, or less in an MRI apparatus using a high magnetic field of 1 tesla or more.

The magnet control unit 109 controls a current flowing through a heater 208 such that the amount of liquid helium vaporized by heat and the amount of helium gas liquefied by the cooling capacity of a cooling unit 209 of the cryocooler 107 are equal. Accordingly, the pressure in the helium vessel 203 is controlled to be at a fixed level (for example, 10 kPa).

An injection port 210 for injecting liquid helium into the helium vessel 203 is provided in an upper portion of the helium vessel 203. At the injection port 210, the above-described heater 208, a liquid meter of the liquid helium 207, or the connection terminal 108 for connection with other sensors is disposed. In addition, a constant-pressure valve 211 which emits helium gas outside when the pressure in the vessel reaches a predetermined pressure (for example, 20 kPa) is fixed in the upper portion of the helium vessel 203. In addition, an emergency exhaust hole 213 including a destructive disc 212 which emits a large amount of helium gas immediately in the event of a quench is also provided. In addition a seal-off valve 214 for evacuation of the vacuum chamber 201 is provided on the side surface of the vacuum chamber 201.

<Cooling Excitation of a Superconducting Magnet>

In the first embodiment, only tests which can be performed at room temperature are done in a factory after manufacturing and assembling the superconducting magnet 101 of the MRI apparatus in the factory, and the superconducting magnet 101 is transported to the work site, such as a warehouse close to medical facilities as a final installation location. Then, the superconducting magnet 101 performs cooling, excitation, and training at the location. After confirming the completion of training, the superconducting magnet 101 is demagnetized and transported to the medical facilities in a cooled state. In the medical facilities, the superconducting magnet 101 is excited after the supply of liquid helium.

Accordingly, since training work in medical facilities can be avoided in the process of installing the superconducting magnet 101 in the medical facilities, it is possible to move to the operational state only with reliable work processes.

In addition, since the superconducting magnet is transported to the medical facilities in a cooled state, the amount of installation work in the medical facilities becomes a minimum. Therefore, there is an advantage in that it is possible to meet replacement demands for MRI apparatuses in a short time.

Hereinafter, the work flow of manufacturing, cooling and excitation, and installation of the MRI apparatus of the present embodiment will be described using FIG. 3.

The MRI apparatus, including the superconducting magnet 101, is manufactured and assembled in a manufacturer's factory (step 401). The manufacture of the superconducting magnet 101 is optimally performed in a place which is optimal for executing a cutting or welding process of a stainless steel material of the superconducting magnet 101, coiling of a superconducting wire, and burying the coil with resin, and the test, for example, in a manufacturer's factory. After assembly, a leak test for checking whether or not there is a leaking spot, such as a pinhole, in the vacuum chamber 201 and the helium vessel 203 is performed in the manufacturer's factory. Specifically, the seal-off valve 214 of the vacuum chamber 201 of the superconducting magnet 101 is connected to a vacuum pump to evacuate the vacuum chamber 201 until the inside reaches a predetermined pressure (for example, 1 Pa or less). In addition to the leak test, items which can be tested at room temperature, for example, a test for checking a superconducting coil circuit constant is performed (step 402). After determination of test pass or fail at room temperature, acceptable products are packed and shipped in the evacuated state (step 403).

The packed superconducting magnet 101 is transported to the work site, such as a warehouse located in the relatively vicinity of medical facilities where the superconducting magnet 101 is finally installed, by road or by ship and is then temporarily installed (steps 404 and 405). In this work site, cooling and excitation are performed.

The superconducting magnet 101 temporarily installed at the work site is evacuated again (step 406). Then, gas molecules in the air adhering to the wall surface of the helium vessel 203 of the superconducting magnet 101 or the surface of a multilayer sheet for heat insulation (super insulator) built into the vacuum chamber 201 during the transportation float to the vacuum layer 202 gradually, and the degraded degree of vacuum is improved again.

When the pressure of the vacuum layer 202 reaches a predetermined pressure with a gap of 1 Pa or less, the helium vessel 203 in which the main superconducting coil 205 and the shielded superconducting coil 206 are disposed is cooled. After cooling, liquid helium is filled (steps 407 and 406). As a cooling method, any one of the following three methods is used.

The first method is that liquid nitrogen is injected through the injection port 210 and is cooled to 77 Kelvin temperature which is a boiling point of liquid nitrogen, then it is replaced with helium gas, and finally liquid helium is injected for cooling to 4.2 Kelvin temperature. The second method is that helium gas cooled to, for example, 20 Kelvin temperature is injected through the injection port 210 and circulated through the helium vessel 203, helium gas is recovered through the emergency exhaust hole 213, and liquid helium is injected when the helium vessel 203 is cooled to the temperature of the cooled helium gas and is cooled to 4.2 Kelvin temperature. The third method is that the cryocooler 107 is operated to cool the helium vessel 203 with the cooling power and the helium vessel 203 is filled with liquid helium finally. Each of the first to third methods has an advantage, and any method may be used in the present embodiment.

The superconducting magnet 101 which is completely cooled is filled with liquid helium and is then left uncontrolled for 24 hours (step 908). This is to sufficiently cool the main superconducting coil 205 and the shielded superconducting coil 206, which are laminated and wound around the bobbin and fixed by resin, up to their deepest parts. Stainless steel of the coil bobbin material of the main superconducting coil 205 and the shielded superconducting coil 206, a superconducting wire formed of copper as a main material, and epoxy resin which fixes a superconducting wire have different thermal contraction rates, and therefore, thermal contraction distortion (structural distortion) occurs due to cooling and filling of liquid helium in steps 407 and 408.

After 24 hours, a power lead is inserted into the injection port 210 of the superconducting magnet 101 to connect a power lead terminal portion to an excitation power supply (step 109). A current flowing through the main superconducting coil 205 and the shielded superconducting coil 206 rises according to a current increase rate set in advance (step 910). By this current supply, one main superconducting coil 205 is electromagnetically attracted to the other main superconducting coil 205 and receives a repulsive force for the superconducting coil 206 in the neighborhood. Then, electromagnetic force distortion occurs in the superconducting coils 205 and 206.

Some energy of thermal contraction distortion at the time of cooling occurring in steps 407 and 408 and electromagnetic force distortion occurring in step 410 are released due to epoxy resin cracking, which occurs during the excitation before reaching the rated current (for example, 500 A), and slight movement of a superconducting wire. The movement of the superconducting wire causes the superconducting wire to be locally heated. As a result, since a part of the main superconducting coil 205 or the shielded superconducting coil 206 changes to a normal conducting state, a quench occurs (step 411). Since a quench occurs in the phase of cooling and excitation as described above, energy of the thermal contraction distortion at the time of cooling and the electromagnetic force distortion at the time of excitation is released. Therefore, a quench after operating the MRI apparatus can be prevented. This is called training of the superconducting magnet 101.

When a quench occurs, the liquid helium 207 is vaporized by heating of the superconducting coils 205 and 206, and a large amount of helium gas is exhausted through the low-pressure valve 211 and the emergency exhaust hole 213.

Then, the process returns to step 408 in which the helium vessel 203 is filled with liquid helium again, and a quenched superconducting coil portion is sufficiently cooled after a predetermined time (for example, at least 12 hours, preferably 24 hours or more).

After cooling, a power lead is inserted again as in steps 409 and 410 in order to connect an excitation power supply to the main superconducting coil 205 and the shielded superconducting coil 206, so that a current flows through the main superconducting coil 205 and the shielded superconducting coil 206. When a quench occurs again, the process returns to step 408 to repeat the training (step 411).

Thus, energy of the thermal contraction distortion and the electromagnetic force distortion is released by repeating the quench. Usually, since it is difficult to predict that the total distortion energy is released if how many times a quench occurs, the steps 408 to 411 are repeated by trial and error for each apparatus.

When the current of the main superconducting coil 205 reaches a 500-A rated current by repeating the steps 408 to 411 and a magnetic field of 1 tesla is generated in the imaging space 103, the excitation is completed (step 412).

By the known technique, the main superconducting coil 205 and the shielded superconducting coil 206 are made to form a closed loop, and the power lead is disconnected to shift to a persistent current mode operation (step 413).

Then, the completion of training is checked. That is, they are kept and stand still in a persistent current mode state for a predetermined time (for example, 24 hours) to confirm that a quench does not occur (step 414). In the meantime, tests for checking the performance of the superconducting magnet 101, such as the stability of the magnetic field strength or the magnetic field homogeneity, are executed.

As described above, the training ends, and the superconducting coils 205 and 206 are demagnetized to transport them from the work site to medical facilities. Specifically, the power lead is inserted again into the injection port 210 to connect the excitation power supply to the superconducting coils 205 and 206, so that the superconducting coils 205 and 206 are demagnetized (step 415). After demagnetization, the superconducting magnet 101 is stored until the day of transport to medical facilities in accordance with the installation schedule in the medical facilities while maintaining the temperature of the helium vessel 203 (step 416).

During the storage, the superconducting magnet 101 is stored in a state where the cryocooler 107 and the magnet control unit 109 are operated. Therefore, since the amount of liquid helium in the helium vessel 203 is maintained, the superconducting magnet 101 can be maintained at the liquid helium temperature of 4.2 Kelvin. When power for operating the cryocooler 107 cannot be acquired or when the operation of the cryocooler 107 stops due to a blackout, liquid helium is supplied through the injection port 210 so that the superconducting magnet 101 maintains the liquid helium temperature.

Figure 4:
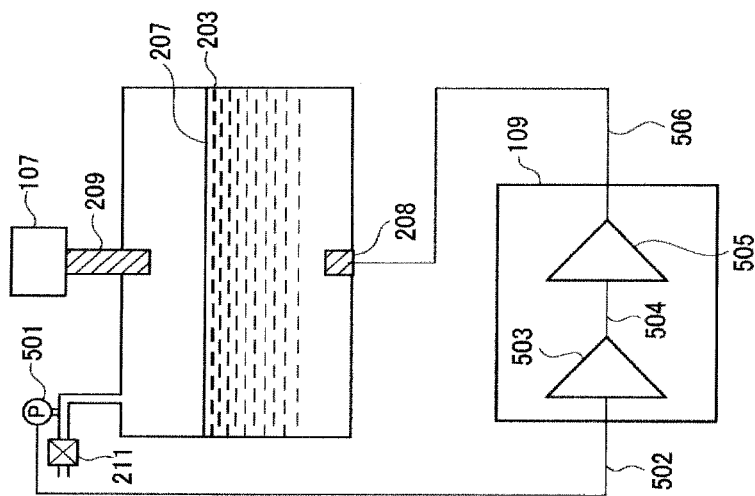
FIG. 4 is a block diagram showing the configuration used to maintain the temperature and the pressure of a helium vessel 203 when stored in the first embodiment.

The operation when storing the superconducting magnet 101 while maintaining the cooling state of the superconducting magnet 101 by the cryocooler 107 and the magnet control unit 109 will be described using FIG. 4. The cooling unit 209 of the cryocooler 107 has a predetermined cooling capacity (for example, 1 W). In the case of cooling capacity of 1 W, 14 liters of helium gas are cooled for 1 minute to return to the helium vessel 203 as 0.02 liter of liquid helium. As a result, the temperature of the helium vessel 203 is maintained.

When the helium gas is changed to liquid helium by the cryocooler 107, the volume reduced to about 1/700. Accordingly, the pressure of the helium vessel 203 is reduced. A pressure sensor 501 which detects the internal pressure of the helium vessel 203 is provided in the helium vessel 203. If the pressure of the cryogenic vessel 203 is reduced, the pressure signal voltage 502 is also reduced. The magnet control unit 109 includes an amplification and inverting circuit and a heater current driving circuit 505. The pressure signal voltage 502 is processed by the amplification and inverting circuit 503 and is then converted into a driving current of the heater 208 by the heater current driving circuit 505. That is, when the pressure signal voltage 502 tends to decrease, an output signal voltage 504 of the amplification and inverting circuit 503 tends to increase. Accordingly, the driving current of the heater 208 also increases. The heater 208 increases the pressure of the helium vessel by heating and vaporizing liquid helium. As a result, the pressure in the helium vessel 203 is maintained constant.

As a specific example, assuming that the resistance of the heater 208 is 25 Ω and a driving current 506 is 100 mA, heat generated by the heater 208 becomes 250 mW. Accordingly, 0.005 liter of liquid helium is vaporized every minute. 0.005 liter of liquid helium becomes 3.5 liters of helium gas which is about 700 times by their volume ratio, and this increases the pressure of the helium vessel 203. The pressure increase causes an increase in the output signal voltage 502 of the pressure sensor 501, and this is input to the magnet control unit 109. Accordingly, since a negative feedback loop through the magnet control unit 109 and the heater 208 is formed by the pressure of the helium vessel 203, the pressure of the helium vessel 203 converges on fixed pressure.

By operating the cryocooler 107 and the magnet control unit 109 as described above, the superconducting magnet 101 can be stored while maintaining the temperature and the pressure of the liquid helium vessel 203.

After the storage, the superconducting magnet 101 is transported to medical facilities as a final installation location. In this case, the superconducting magnet 101 is transported in a state where the helium vessel 203 is filled with liquid helium 100% in order to maintain the cooling state (step 417). When a transportation time is long (for example, 10 days), a method of maintaining the cooling state is performed en route so that the temperature of the helium vessel 203 does not become higher than the liquid helium temperature of 4.2 Kelvin. For example, liquid helium is injected en route or the cryostat is operated en route (step 418).

In the medical facilities, the installation process is performed, and liquid helium is supplied through the injection port 210. Then, a power lead is inserted to supply a current from the excitation power supply to the superconducting coils 205 and 206. When the current reaches a rated current, the superconducting coils 205 and 206 are made to form a closed loop, and the power lead is disconnected (step 419). Then, the superconducting magnet generates a predetermined magnetic field so that the MRI apparatus can operate.

In step 419 of excitation performed in the medical facilities, it is not necessary to perform training. This is because the training is sufficiently performed at the work site before transportation in steps 408 to 411 in order to release distortion energy of the superconducting magnet and the superconducting magnet is stored and transported in a state where the liquid helium temperature is maintained as 4.2 Kelvin by cooling and accordingly, distortion does not occur again.

In addition, when performing the installation process in medical facilities, it is not necessary to perform training in which it is difficult to predict how many times a quench occurs. Accordingly, the installation period can be checked in advance, and the installation process can be performed in a short time.

In addition, since the training is not performed in medical facilities, vaporization of a large amount of liquid helium due to a quench does not occur. Therefore, surprising hospital employees or neighboring residents by white smoke does not occur.

<Second Embodiment>

Figure 5:
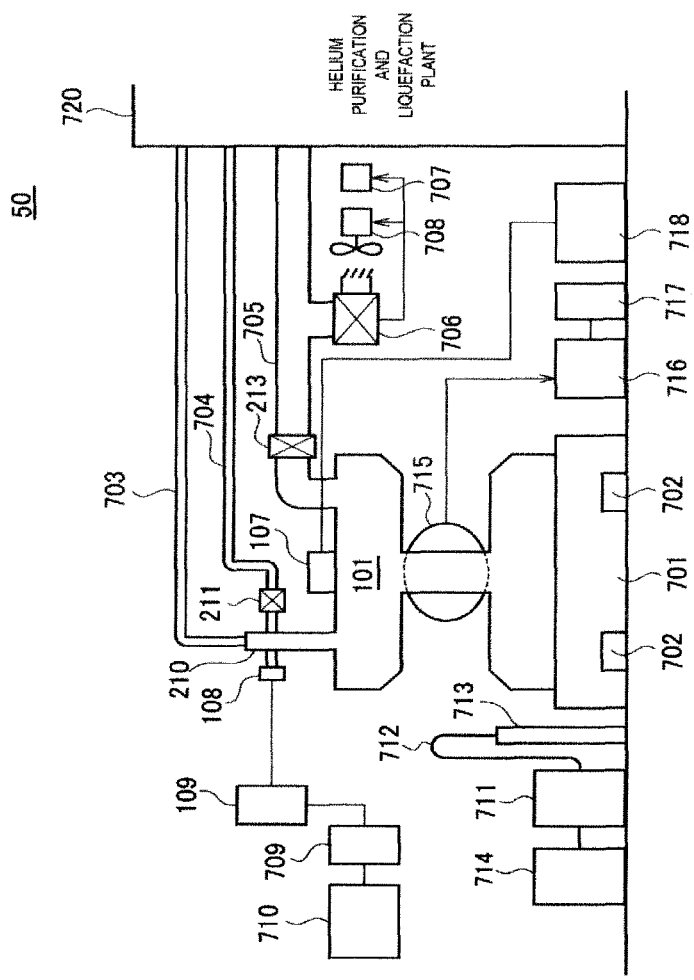
FIG. 5 is a block diagram showing the configuration of a superconducting dock 50 used in a second embodiment.

In a second embodiment, a dock station in which a plurality of dedicated facilities (superconducting magnet dock) 50 shown in FIG. 5 are placed is provided in order to perform training of superconducting magnets. The superconducting magnet 101 of the MRI apparatus manufactured in the factory is first transported to the superconducting magnet dock station to execute cooling, excitation, and training. After confirming the completion of training, the superconducting magnet 101 is demagnetized and transported to medical facilities in a cooled state. In the medical facilities, the superconducting magnet 101 is excited after the supply of liquid helium.

The superconducting magnet dock station is provided in a helium purification and liquefaction plant in order to supply and recovery the liquid helium.

First, the configuration of the superconducting dock station will be described. In the superconducting dock station, the plurality of superconducting docks 50 are provided at distances therebetween so that the plurality of superconducting magnets 101 can be cooled and excited without interfering with each other.

The superconducting dock 50 includes a wooden magnet frame 701, a refrigerant injection adapter 703, a recovery pipe 704 of refrigerant gas at the normal time, and a large-diameter pipe 705 for recovery of refrigerant gas in the event of a quench. The injection adapter 703, the recovery pipe 704, the large-diameter pipe 705 are connected to a helium purification and liquefaction plant 720. A refrigerant is supplied to the injection adapter, refrigerant gas recovered from the recovery pipe 704 and the large-diameter pipe 705 is purified and liquefied in the plant 720.

In addition, an excitation power supply unit 711, a cable 712, and a power lead adapter 713 for performing an excitation operation are provided in the superconducting dock 50. A computer 714 which records the value of a current flowing through the superconducting magnet and the like is connected to the power supply unit 711.

Moreover, in the superconducting dock 50, a field camera (NMR sensor) 715 disposed at the center of the magnetic field space of the superconducting magnet 101, an NMR spectrometer 716 which processes the signal, and a magnetic field calculation computer 717 in which a processing program for calculating the stability of the magnetic field strength or the magnetic field homogeneity is installed are provided as apparatuses which measure the magnetic field homogeneity and the strength of the magnetic field generated by the superconducting magnet 101 after training is completed.

In addition, a compressor 718 for driving the cryocooler 107 is provided as a facility for maintaining the cooling state of the superconducting magnet 101. In addition, a computer 109 for recording an output of the magnet control unit 109 and a display 710 are disposed.

In the superconducting magnet dock 50 with such a configuration, the superconducting magnet 101 is placed on the wooden magnet frame 701. Accordingly, the superconducting magnet 101 is separated about 30 cm from the floor in order to reduce the influence of a magnetic material on the reinforced concrete floor. A forklift work hole 702 is provided in the magnet frame 701 so that movement in the superconducting magnet dock station becomes easy. In addition, sufficient workspace is secured near the superconducting magnet 101 so that various kinds of operations are easily done. This workspace also functions as a safe space for eliminating the influence of surrounding magnetic materials when a magnetic field is generated.

The injection adapter 703 of the superconducting dock 50 is connected to the injection port 210 of the superconducting magnet 101, and a refrigerant for cooling the superconducting magnet is injected from the helium purification and liquefaction plant 720.

The constant-pressure valve 211 of the superconducting magnet 101 is opened, and the pipe 704 formed of stainless steel is connected to the constant-pressure valve 211. The large-diameter pipe 705 formed of stainless steel is connected to the emergency exhaust hole 213 through which a large amount of refrigerant gas is emitted in a short time in the event of a quench. The vaporized refrigerant is recovered through the recovery pipe 704 and the large-diameter pipe 705 and is sent to the helium purification and liquefaction plant 720 so as to be purified and liquefied.

Since the injection adapter 703, the recovery pipe 704, and the large-diameter pipe 705 are formed of stainless steel, it is possible to prevent the corrosion due to condensation or the mixing of impurities with the refrigerant gas which occurs due to passing of the refrigerant gas.

The diameter of the large-diameter pipe 702 is a large diameter of 30 cm, for example, so that a large amount of refrigerant gas can pass through the large-diameter pipe 702 in the event of a quench. The large-diameter pipe 702 includes a constant-pressure valve 706. If the pressure of the large-diameter pipe 705 rises due to failure of the helium purification and liquefaction plant, for example, the constant-pressure valve 706 is opened with predetermined safe pressure (for example, 42 kiloPascals) to emit the refrigerant gas into the air. As a result, a pressure increase equal to or larger than a predetermined value can be prevented. A ventilating fan 708 and an alarm 707 are disposed near the constant-pressure valve 706. When the constant-pressure valve 706 operates, the alarm 707 gives an alarm and the ventilating fan 708 operates to quickly diffuse the refrigerant into the air. As a result, emission of the refrigerant gas into the air as white smoke and being mistaken for a fire or the like are prevented.

A computer 709 is connected to the magnet control unit 109 connected to the connection terminals 108 of various magnet sensors. The computer 709 displays an output of the magnet sensor on the display 710 in an enlarged manner. Therefore, the operator near the superconducting magnet 101 can check it easily.

The excitation power supply unit 711 for performing an excitation operation is separated from the superconducting magnet 101 by a distance (for example, 7 meters) not influenced by the magnetic field generated by the superconducting magnet 101. The power lead adapter 713 is inserted into the injection port 201 after the injection adapter 703 is disconnected when cooling is completed, and is connected to the main superconducting coil 205 and the shielded superconducting coil 206 to supply a current for excitation. The computer 714 which records the value of a current flowing through the superconducting magnet and the like is connected to the power supply unit 711.

In addition, the field camera 715 and the NMR spectrometer 716 which process the signal measure the magnetic field homogeneity and the strength of the magnetic field generated by the superconducting magnet 101 at the time of rated persistent current operation after training is completed. A processing program for calculating the stability of the magnetic field strength or the magnetic field homogeneity is installed in the computer 717.

Hereinafter, the work flow of manufacturing, cooling and excitation, and installation of the MRI apparatus of the second embodiment will be described using FIG. 3 in the same manner as in the first embodiment.

Figure 3:
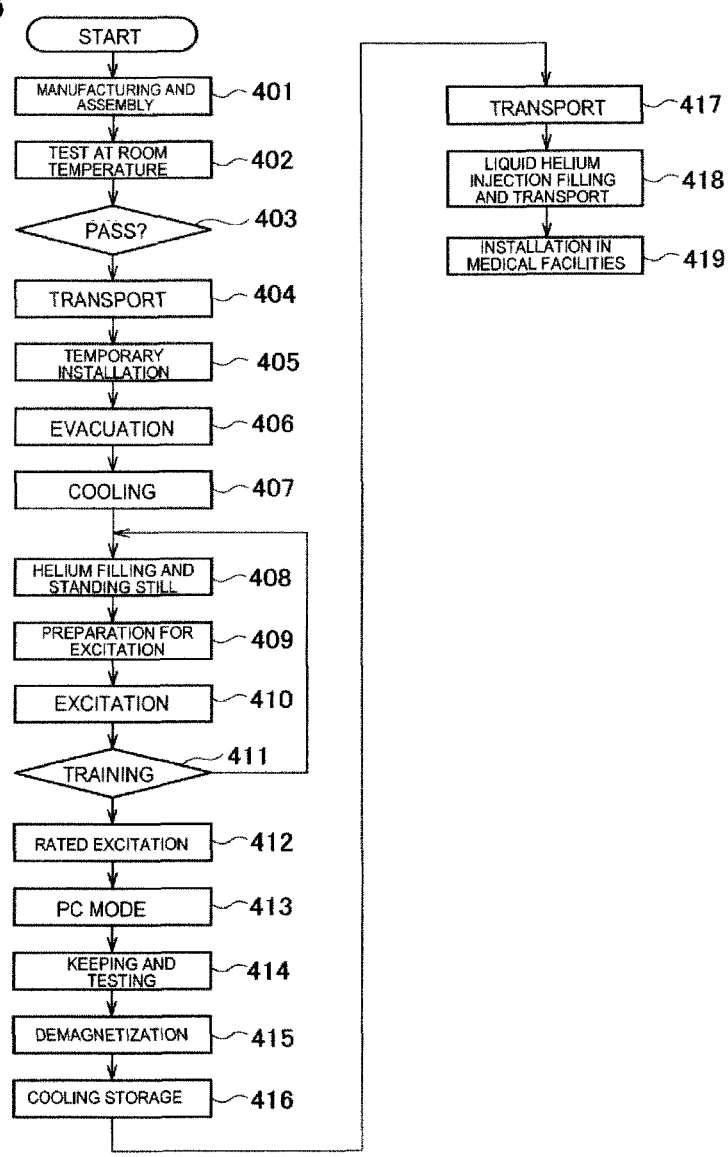
FIG. 3 is a flow showing a method of cooling and excitation of the superconducting magnet of a first embodiment.

The operation flow in FIG. 3 is a method of minimizing the cost required for ensuring of the quality and the work of a superconducting magnet by executing, at best places, each process from manufacturing of the superconducting magnet to installation in medical facilities. That is, the process which needs a large amount of helium gas and liquid helium for cooling, excitation, and training of a superconducting magnet is executed in the superconducting dock station, the superconducting magnet is demagnetized after confirming the completion of the training, and the superconducting magnet is temporarily stored while maintaining the cooling state and is transported to medical facilities. When a period of transportation to medical facilities is long, liquid helium is supplied en route so that the cooling state can be maintained as long as possible.

Therefore, similarly to the first embodiment, undecided training work in a required period in medical facilities can be avoided when installing the superconducting magnet 101 in the medical facilities. Accordingly, it is possible to move to the operational state in a decided working time. In addition, since the superconducting magnet is transported to the medical facilities in a cooled state, the amount of installation work in the medical facilities becomes a minimum. Therefore, there is an advantage in that it is possible to meet replacement demands for MRI apparatuses in a short time. In addition, in the second embodiment, it is easy to supply a large amount of helium gas and liquid helium required at the time of cooling, excitation, and training, and the cost can be reduced by performing the process in the dedicated facility (superconducting dock 50) which can recover and reuse the helium gas.

As shown in FIG. 3, the superconducting magnet 101 is first assembled in the manufacturer's factory, tests possible at room temperature are executed, and test pass or fail at room temperature is determined. Then, acceptable products are packed and shipped and are transported to the location (superconducting dock 50) for cooling and excitation by land or by sea. These processes are the same as steps 401 to 404 in FIG. 3 in the first embodiment. In the second embodiment, the superconducting magnet 101 is transported to the superconducting dock station by this transportation and is temporarily installed in the superconducting dock 50 (step 405). That is, the superconducting magnet 101 is mounted on the frame 701 in FIG. 5. In addition, the injection adapter 703, the recovery pipe 704, and the large-diameter pipe 705 are connected to the injection port 210, the constant-pressure valve 211, and the emergency exhaust hole 213 of the superconducting magnet 101, respectively.

In the same manner as in the first embodiment, the superconducting magnet 101 temporarily installed at the superconducting dock 50 is evacuated again (step 406), and the superconducting magnet 101 is cooled and filled with liquid helium when the pressure reaches a predetermined pressure (steps 907 and 408).

In the second embodiment, this cooling operation is performed using a facility of the superconducting dock 50, unlike the first embodiment. As a first cooling method, a refrigerant (for example, liquid nitrogen) is injected from the injection adapter 703 into the injection port 210, and the temperature of the helium vessel 203 is cooled to 77 Kelvin. Then, the helium gas is supplied from the injection adapter 703 to the injection port 210 for replacement. Finally, the liquid helium is injected from the injection adapter 703 into the injection port 210 for cooling to 4.2 Kelvin temperature. During this period, the refrigerant gas exhausted from the constant-pressure valve 211 is recovered through the recovery pipe 704 and is purified and liquefied in the helium purification and liquefaction plant 720 so as to be reused.

As a second cooling method, cooled helium gas is injected from the injection adapter 703 into the injection port 210 and is made to circulate through the helium vessel 203, and the helium gas is recovered from the emergency exhaust hole 213 through the large-diameter pipe 705. Finally, liquid helium is injected from the injection adapter 703 into the injection port 210 and is cooled to 4.2 Kelvin temperature. The liquid helium recovered from the large-diameter pipe 705 is purified and liquefied in the helium purification and liquefaction plant 720 so as to be reused.

A third method is that the compressor 718 is connected to the cryocooler 107, the cryocooler 107 is operated to cool the helium vessel 203 with the cooling power, and finally liquid helium is injected from the injection adapter 703 to the injection port 210 so that the helium vessel 203 is filled with liquid helium.

Thus, since the cooling operation is performed in the superconducting dock 50, it is not necessary to transport the cooled helium gas or liquid helium from the helium purification and liquefaction plant 720. Accordingly, a refrigerant is efficiently supplied. In addition, there is no loss due to transportation of liquid helium, and the helium gas emitted from the superconducting magnet 101 can be recovered by the helium purification and liquefaction plant 720 so as to be reused.

Then, the completely cooled superconducting magnet 101 is filled with liquid helium and left uncontrolled for 24 hours to sufficiently cool the superconducting coils 205 and 206 up to their deepest parts, and then the training in steps 109 to 411 is performed. At this time, it is assumed that the injection adapter 703 and the large-diameter pipe 705 are connected to the superconducting magnet 101. This is done so that a large amount of helium gas vaporized in the event of a quench in training can be recovered and a refrigerant can be easily injected from the injection adapter 703 when returning to step 408 to fill helium again.

A specific operation of the training is the same as in steps 409 to 411 of the first embodiment. The power lead adapter 713 is inserted into the injection port 210 of the superconducting magnet 101, and the excitation power supply is connected to the superconducting coils 205 and 206 so that a current flows through the superconducting coils 205 and 206. The current value is increased according to the current increase rate set in advance. In the event of a quench caused when thermal contraction distortion and electromagnetic force distortion are released, a large amount of helium gas is emitted from the emergency exhaust hole 213. In the present embodiment, the helium gas is recovered through the large-diameter pipe 705 and is purified and liquefied by the helium purification and liquefaction plant 720.

The process returns to step 408 in which liquid helium is injected again from the injection adapter 703 to the injection port 210 to fill the helium vessel 203 with the liquid helium and the superconducting magnet is left uncontrolled for a predetermined time (24 hours) (step 408). The power lead adapter 713 are inserted again so that a current is supplied to the superconducting coils 205 and 206, the current value is increased at a predetermined increase rate (steps 409 and 410). In the event of a quench (step 411), steps 408 to 910 are repeated.

If the current of the superconducting coils 205 and 206 reaches a rated current, the superconducting coils 205 and 206 shift to a persistent current mode operation and are kept and stand still in the persistent current mode state for 24 hours, for example, to confirm the completion of the training (step 412-414). In the meantime, tests for checking the performance of the superconducting magnet 101, such as the stability of the magnetic field strength or the magnetic field homogeneity, are executed. Then, the superconducting coils 205 and 206 are demagnetized, and the cryocooler 107 and the magnet control unit 109 are operated to store the superconducting magnet 101 in a cooling state (steps 415 and 416).

When transporting the superconducting magnet 101 from the superconducting dock station to the medical facilities as a final installation location, the superconducting magnet 101 is moved in a state where the helium vessel 203 is filled with liquid helium 100% (step 418). When a transportation time is long, a method of maintaining the cooling state is performed en route so that the temperature of the helium vessel 203 does not become higher than the liquid helium temperature of 4.2 K. For example, liquid helium is injected (step 416). In the medical facilities, the installation process is performed, and the rated current is supplied to the superconducting coils 205 and 206 to excite them (step 419). These procedures are the same as those in the first embodiment.

In step 419 of the installation process performed in the medical facilities, it is not necessary to perform training. This is because the training is sufficiently performed at the work site before transportation in steps 408 to 411 in order to release distortion energy of the superconducting magnet and the superconducting magnet is stored and transported in a cooled state and accordingly, distortion does not occur again. Accordingly, since the training a required time for which is not decided does not need to be performed in medical facilities, the installation period can be checked in advance, and the installation process can be performed in a short time. In addition, since the training is not performed in medical facilities, vaporization of a large amount of liquid helium due to a quenching does not occur. Therefore, surprising hospital employees or neighboring residents does not occur.

In addition, by performing the training in the superconducting dock station, it is possible to easily supply a large amount of liquid helium required in the event of a quench. Moreover, since helium gas can be recovered and reused, cost reduction can be realized.

In addition, when the transportation period is long and it is not possible to supply liquid helium to the liquid helium vessel 203 in the course of transportation, the temperature of the helium vessel 203 may become higher than 4.2 K. In this case, the helium vessel 203 needs to be cooled again to the liquid helium temperature in the installation process in medical facilities. Then, thermal contraction distortion may occur due to re-cooling and a quench (training) may occur accordingly. Therefore, in the case of performing re-cooling, re-training in which steps 408 to 412 in FIG. 3 are performed is executed in the installation process. Even if re-training is performed, distortion can be released with the small number of times of training (number of times of quench) since thermal contraction distortion occurring due to a temperature increase during transportation is small. Therefore, an undecided training period in medical facilities can be shortened.

In addition, although the open-structure superconducting magnet 101 using a vertical magnetic field method, in which cryostats of the superconducting magnet 101 are divided into the upper cryostat 104 and the lower cryostat 105, has been described as an example in the above embodiments, the invention is not limited to the superconducting magnet 101 with this shape, and it is needless to say that the invention can also be applied to a tunnel type superconducting magnet 101 using a horizontal magnetic field method.

REFERENCE SIGNS LIST

101: superconducting magnet
102: subject
103: imaging space
107: cryocooler
109: magnet control unit
111: gradient magnetic field coil
112: gradient magnetic field power supply
113: high-frequency coil
114: high-frequency power supply
115: detection coil
116: high-frequency amplifier circuit
117: computer
201: vacuum chamber
203: helium vessel
205: main superconducting coil
206: shielded superconducting coil
208: heater
406: evacuation step
407: cooling step
410: excitation step
411: training
416: cooling storage step 501: pressure sensor
701: frame
703: injection adapter
704: recovery pipe
705: large-diameter pipe

The invention claimed is:

1. A dock for superconducting magnet excitation comprising:
   a plant for condensing helium gas to liquid helium;
   a frame on which a superconducting magnet is mounted;
   a supply pipe used to send liquid helium from the plant to the superconducting magnet;
   at least two recovery pipes, with different diameters, to send helium gas from the superconducting magnet to the plant;
   a power supply for supplying an excitation current to the superconducting magnet; and
   a power lead which connects the power supply to the superconducting magnet;
   a constant-pressure valve, which is opened when the pressure in the recovery pipe exceeds predetermined pressure, provided in the recovery pipe with the larger diameter; and
   a fan for diffusing helium gas emitted when the constant-pressure valve is opened,
   wherein the recovery pipe with a larger diameter connected to an emergency exhaust hole for exhausting helium gas, which evaporates in the superconducting magnet in the event of a quench, to the outside.

2. A dock for superconducting magnet excitation comprising:
   a plant for condensing helium gas to liquid helium;
   a frame on which a superconducting magnet is mounted;
   a supply pipe used to send liquid helium from the plant to the superconducting magnet;
   a recovery pipe used to send helium gas from the superconducting magnet to the plant;
   a power supply for supplying an excitation current to the superconducting magnet; and
   a power lead which connects the power supply to the superconducting magnet;
   a constant-pressure valve, which is opened when the pressure in the recovery pipe exceeds predetermined pressure, provided in the recovery pipe; and
   a fan for diffusing helium gas that is emitted when the constant-pressure valve is opened.

3. The dock for superconducting magnet excitation according to claim 2,
   wherein the recovery pipe comprises at least two recovery pipes with different diameters used to send the helium gas from the superconducting magnet to the plant, and
   the recovery pipe with a larger diameter is connected to an emergency exhaust hole for exhausting helium gas, which evaporates in the superconducting magnet in the event of a quench, to the outside.

4. The dock for superconducting magnet excitation according to claim 3,
   wherein the constant-pressure valve which is opened when the pressure in the recovery pipe exceeds predetermined pressure is provided in the recovery pipe with the larger diameter.

* * * * *